United States Patent [19]

Brown et al.

[11] 4,433,570
[45] Feb. 28, 1984

[54] MECHANICAL SHOCK MACHINE

[75] Inventors: Jack M. Brown, Costa Mesa; Terrance S. Miller, El Toro, both of Calif.

[73] Assignee: B & W Engineering Corporation, Costa Mesa, Calif.

[21] Appl. No.: 334,283

[22] Filed: Dec. 24, 1981

[51] Int. Cl.³ .............................................. G01N 3/30
[52] U.S. Cl. ..................................................... 73/12
[58] Field of Search ........................................... 73/12

[56] References Cited

U.S. PATENT DOCUMENTS 2,696,105  12/1954  Mackas ................................... 73/12
3,557,603  1/1971  Carr ....................................... 73/12

*Primary Examiner*—Anthony V. Ciarlante
*Attorney, Agent, or Firm*—Edwin A. Oser

[57] ABSTRACT

A mechanical shock machine may consist of a small bench-top device with a built-in pneumatic isolator, the working parts of which are enclosed to prevent injury to the operator. The device to be tested is placed on the test platen of the mechanical shock machine and retained there by mechanical clamps or by a viscous fluid. A bullet-like object is then accelerated toward the underside of the test platen, striking it in free or ballistic flight. The strike target contains a resilient pad. Different thicknesses of this pad produce different durations of the shock pulse, with thicker pads relating to longer duration pulses. A skirt near the outer edge of the test platen is suspended in a viscous shock fluid that absorbs the energy of the bullet strike without a major displacement of the test platen, and reduces second strike effects and ringing of the assembly. The motor inducing acceleration to the bullet is contained and its motion captured within the enclosed volume of the shock machine. The bullet is captured after it has expended most of its energy to the platen assembly by a guard ring and snubber. Return of the motor, bullet and platen to their initial position before initiation of the shock pulse may be by powered reversal or by gravity, or a combination thereof.

4 Claims, 4 Drawing Figures

MECHANICAL SHOCK MACHINE

BACKGROUND OF THE INVENTION

Various mechanical shock machines are known, which develop G forces by the controlled collision of a hammer and anvil system. Various interface materials may be used to modify the duration and shape of the shock induced by the collision. Usually the device or component to be tested is mounted on the moving or hammer part, although the opposite may be true where severe shock levels are required.

However, most mechanical shock generating machines produce secondary physical stimuli such as damped vibration, secondary shocks and off-axis motion, which, of course, is highly undesirable. This is particularly true where shock levels above 500 G's are required and such undesirable vibrations may damage the device under test.

A G is equal to 978 cm/sec$^2$ at 0 degrees latitude. Thus, a G is defined as the acceleration due to the gravity on earth.

Furthermore, the physical impact associated with the shock pulse generated by the machine may cause injury to personnel if the machine is not properly protected by shields or electronic safety devices. This is particularly true because the impact occurs in many cases in a location accessible to an operator. An example of such a shock generating machine is shown in the U.S. patent to Otera, et al., No. 3,597,960. This machine will generate shocks on the order of 4,000 G's.

It should also be noted that, typically, mechanical shock machines are made with special accelerometers to measure such shocks. A controversy has been generated concerning the propriety of electronically filtering higher frequency components of the shock pulses. This will cause the shaped mechanical pulse to look "clean" even though, in fact, the device under test may be subjected to severe secondary stimuli.

SUMMARY OF THE INVENTION

In accordance with the present invention, there is provided a mechanical shock generating machine. The machine basically provides a platen for mounting a component or device to be shock-tested. Means are connected to the platen for yieldably mounting it and for causing it to move under the impact of a mechanical shock. There is further provided a heavy element such as a bullet, having a rounded nose which is adapted to be projected in a ballistic mode, or free flight toward the platen. Finally, means are provided for projecting the bullet with sufficient energy to impart to the platen a predetermined number of G's.

Preferably, a shock pad of a yieldable material is disposed below the platen. This is then impacted by the bullet.

The platen may be provided with a depending skirt such as a cylinder immersed in a viscous fluid. When impacted by the bullet, the platen is capable of moving against the shear action of the viscous fluid which isolates it also from secondary shocks and the like.

The bullet may, for example, be accelerated by energizing an electromagnet which causes its armature to move toward the platen while the bullet rests on it. The motion of the armature is braked when it moves past the magnetic return path. Stop means may be provided for arresting the motion of the armature. The bullet is then in free flight to impact the shock pad of the platen.

The novel features that are considered characteristic of this invention are set forth with particularity in the appended claims. The invention itself, however, both as to its organization and method of operation, as well as additional objects and advantages thereof, will best be understood from the following description when read in connection with the accompanying drawings.

DESCRIPTION OF THE PREFERRED EMBODIMENT

Figure 1:
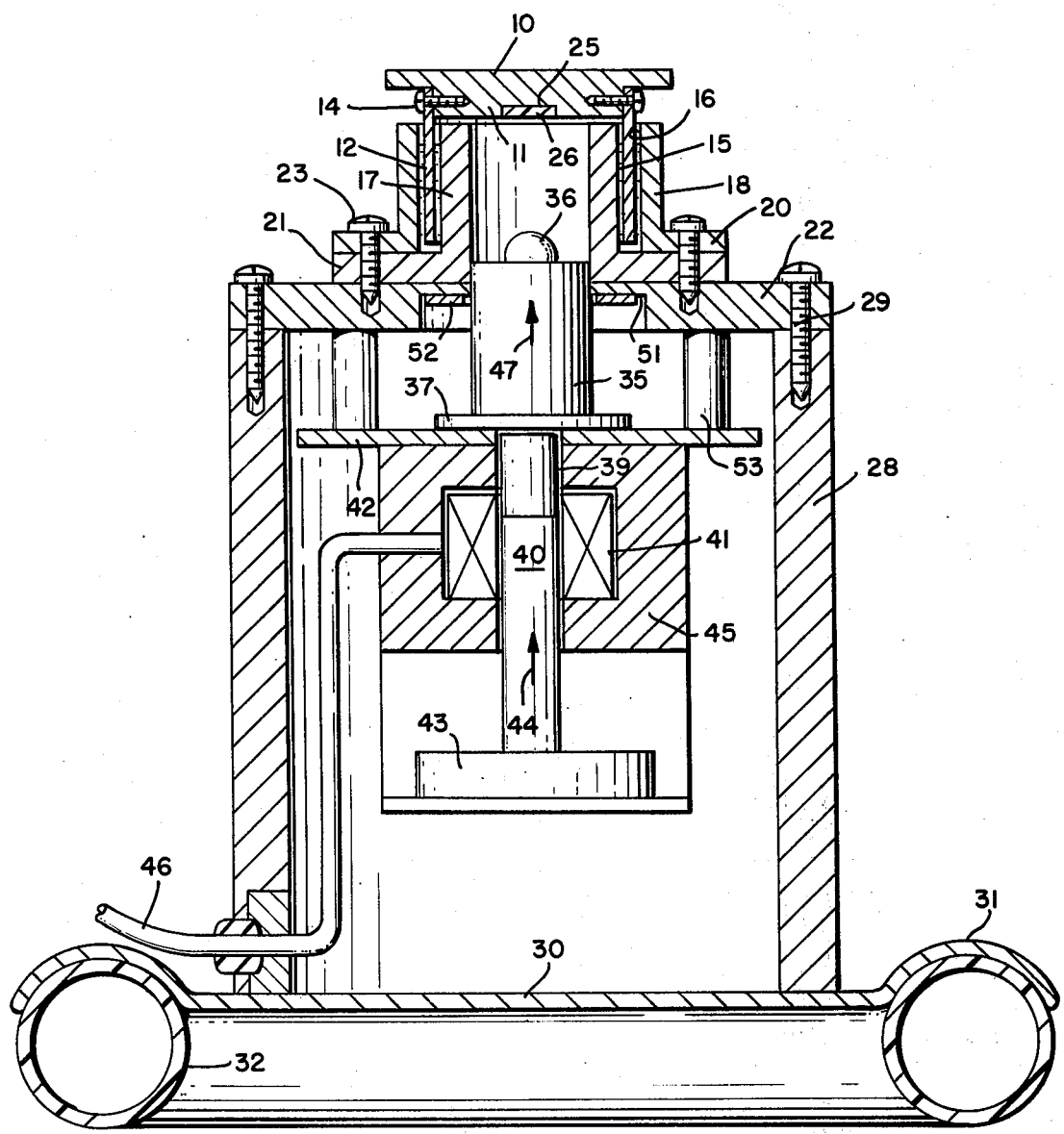
FIG. 1 is a cross-sectional view of the mechanical shock generating machine of the invention.

Referring now to FIG. 1, there is illustrated an embodiment of the present invention. The invention is designed particularly for shock-testing small components or devices in accordance with MIL-STD-883, TM 2002.2, Condition A or B, and MIL-STD-750B, TM 2081(FIST) requirements.

As shown in FIG. 1, the mechanical shock generating machine of the invention includes a platen 10 which may have a reduced central position 11 and which may be circular in outline, as are all the components shown in FIG. 1.

A cylinder 12 depends from the platen 10 and may be secured thereto by bolts 14. The cylinder or skirt 12 is immersed in a viscous fluid 15. This fluid may, for example, consist of a high viscosity oil such as 140 wt. gear oil. However, the viscosity may very between 40 and 300 wt. The skirt 12 and the viscous fluid 15 are disposed in an annular space 16 formed between an inner cylindrical element 17 and an outer cylinder element 18, each having a circular plate 20 and 21, respectively.

The elements 17 and 18 rest upon a face plate or disk 22 to which they are secured by bolts 23, or the like.

The lower surface of the platen 10 is provided with an annular recess 25 in which is disposed a disk-like pad 26 which is yieldable. This shock pad consists of a resilient material such, for example, as silicone rubber. Although the shock pad 26 has been shown in the shape of a flat disk, it may also be formed or shaped to provide a predetermined shock impact.

The platen 10 may, for example, consist of aluminum or magnesium or may be laminated from several materials.

The machine rests on a cylindrical support or tower 28 which in turn is supported by a plate 30 having outwardly curved or convex outer ends 31 to enclose a pneumatic insulation. This insulation may be formed by a rubber doughnut-shaped element or torus 32, which may be filled with compressed air. This, in turn, will mechanically isolate the machine from the desk top on which it may be mounted. The cylinder or tower 28 encloses, together with the cylinder 18, the entire machine, so that it cannot hurt an operator. The face plate 22 is secured to the tower 28 by bolts 29.

The mechanical impact is provided by a heavy element 35 which may have the shape of a bullet having a rounded nose 36. It has an annular ground plate or supporting surface 37 which rests upon an armature 40, which is movable within a coil or inductor 41 to form an electromagnet. The armature has an upper extended plate 42 upon which rests the bullet 35 with its support 37. It has also a somewhat shorter lower foot 43 that includes a portion of the magnetic return for the armature. The entire armature is movable upwardly, as shown by the arrow 44. The coil or inductor 41 is surrounded by a suitable piece of soft iron 45 forming the magnetic return.

A drive bolt 39 of circular cross-section may be provided between the armature 40 and the ground plate 37. It serves the purpose to help lift the bullet 35 when the armature moves upwardly. The drive bolt 39 is guided by the cylindrical aperture within the coil 41 and the magnetic return 45. The bolt 39 may be loose in the armature 41 and return 45, or it may be secured to the armature assembly 40, 42 in any suitable manner. If the bolt is not fastened, it will return by gravity to its original position of FIG. 1 after the armature has moved upwardly.

The entire armature assembly 40, 42, 43, 45 is secured by two connecting members 53 to the lower surface of the face plate 22. The members 53 are secured to the upper surface of the plate 42.

The inductor 41 is energized through a power cable 46 in a manner to be explained in connection with FIG. 2.

Assuming now that the coil 41 is energized for a period of time, this will cause the armature 40 to move upwardly in the direction of arrow 44. Consequently, the bullet 35 also moves upwardly, as shown by the arrow 47, and is pushed in part by the drive bolt 39.

The armature is eventually stopped by the upper surface of the armature foot 43 hitting the lower surface of magnetic return 45. Subsequently, the bullet 35 is now in free flight, or in a ballistic mode.

Eventually the bullet nose 36 impacts the shock pad 26, with the shock pad deforming and transmitting the mechanical shock to the platen 10. Eventually, the platen 10 moves upwardly in the direction of arrow 50. This motion is retarded by the shear action of the viscous fluid 15. Thus, the platen 10 is permitted to rise slowly, due to the shear action of the viscous fluid 15, to prevent secondary shocks and ringing of the platen. At the same time, the platen 10 is mechanically isolated from the possible shock caused by the armature foot 43 impacting the magnetic return 45 and the bullet 35 with its foot 37 impacting a washer 51, which is disposed on the lower recessed surface 52 of the face plate 22.

The pulse duration of the mechanical shock is determined by the thickness of the shock pad 26. A thicker shock pad will produce a pulse or shock of longer duration. The thickness of the shock pad may vary between 50 mils and 0.3 inches. This will, in turn, generate a shock pulse duration of between 0.3 milliseconds and 2.5 milliseconds. The number of G's for a pulse duration of 0.3 milliseconds may be 3,000 G's, and for a pulse duration of 2.0 milliseconds may be as much as 3,500 G's, or more.

With a bigger machine, it will be understood that higher numbers of G's are readily obtainable. The weight of the bullet 35 may be one pound or more.

The shape of the bullet nose 36 is critical. It should be contoured to have a large radius; that is, the nose may be at least partially of spherical shape. The contour may be designed to give more than a single point of impact.

The washer 52 may, for example, consist of rubber. However, as explained before, the platen is insulated by the viscous fluid from the shock that may be produced when the armature hits the washer 52.

It will be understood that the bullet may be accelerated in various ways instead of by a magnetic field, as shown in the preferred embodiment. That is, a large spring may be utilized for accelerating the bullet, or an explosive charge, by firing a cartridge, may trigger the acceleration. Thus a powerful compression spring may be released to accelerate the bullet. Subsequently the spring may be returned to its compressed state, as well as the bullet to its initial position, by an electrically controlled rack and pinion motor. Gravity may also be used, by accelerating the bullet in a generally U-shaped path.

Figure 2:
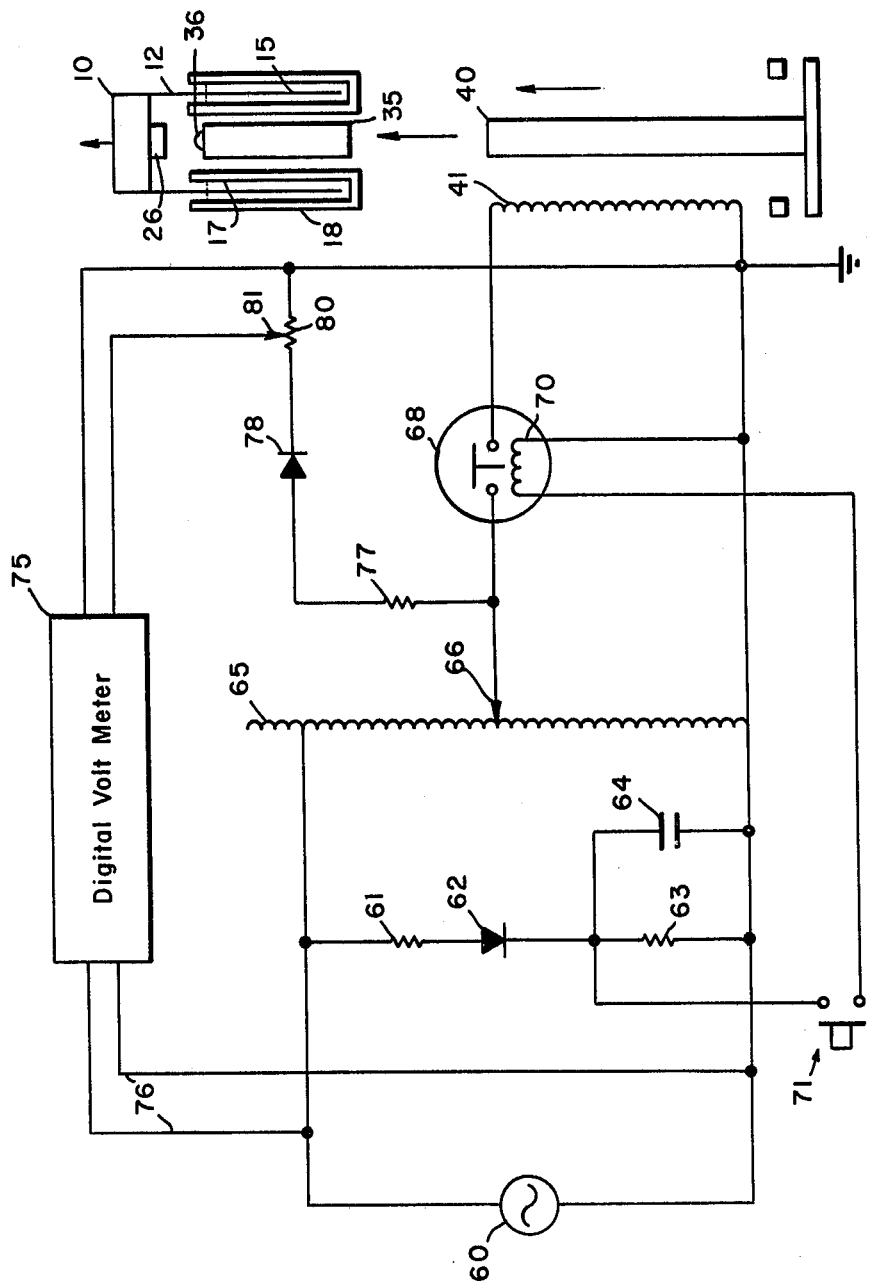
FIG. 2 is a circuit diagram illustrating the electronic circuit for energizing the inductor of the electromagnet which propels the bullet.

Referring now to FIG. 2, there is illustrated an electromagnet 41 including an alternating current source 60. A resistor 61, diode 62, and resistor 63 are serially connected across the voltage source 60. A capacitor 64 is connected across resistor 63. A coil or inductor 41 is driven by an auto transformer 65, a portion of which is connected across the generator 60. A tap 66 on the auto transformer 65 is connected to one terminal of the inductor 41, while the other is connected to ground of the generator 60. A relay 68 may be a solid-state relay which connects the tap 66 to the inductor 41 when the voltage of the generator 60 passes through zero. The relay 68 is energized by a coil 70 when the main switch 71 is closed. This will connect the junction point between diode 62 and resistor 63 to the coil 70 and ground.

The coil 70 is energized by the voltage across capacitor 64. This voltage is rapidly discharged through the coil 70 to determine the period of time the inductor 41 is energized. The diode 62 forms a half wave rectifier. It will be noted that the auto transformer is variable by the tap 66 which determines the voltage applied to 41, which, in turn, controls the G level of the shock. The coil 41 may receive power for a period of 100 milliseconds, depending on the RC constant of the circuit 63, 64.

FIG. 2 also schematically shows the armature 40, the bullet 35, the platen 10, the skirt 12, the viscous fluid 15 and the container for the fluid 17, 18.

A digital volt meter 75 may also be provided, having its input connected across the generator 60 by leads 76. The voltage to be measured is obtained from tap 66 through a resistor 77, diode 78, forming a half-wave rectifier, and resistor 80 connected in series to ground. A tap 81 provides a predetermined voltage which may be applied to the digital voltmeter, the voltage being determined between the tap 81 and ground.

It will be understood that the circuit specifications of the circuit of FIG. 2 may vary according to the design for any particular application. The following circuit specifications are included by way of example only, as suitable for a small shock generating machine for generating shocks in the order of 3,000 G's.

| | |
|---|---|
| Resistor 61 | 160K ohms |
| Resistor 63 | 22K ohms |
| Potentiometer 80 | 100K ohms |
| Resistor 77 | 1 megohm |
| Capacitor 64 | 22 mfd |
| Diode 62 | type 1N4004 |
| Diode 78 | type 1N4004 |
| Solid State Relay 68 | Model Z240 D 10 |

(from Opto 22)

It should be noted that the mechanical shock is in the form of half sine and haversine pulse shapes.

Figure 3:
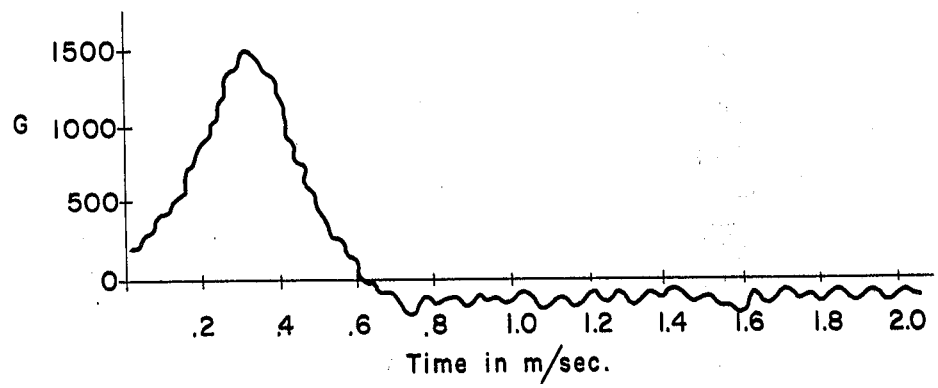
FIGS. 3 and 4 are graphs of shock tests obtained with the shock generating machine of the invention, without and with a filter, respectively.

FIG. 3 is a graph of a shock test obtained with the shock generator machine of the invention as illustrated in FIG. 1. Each vertical dimension of 1 cm corresponds to 500 G's and each horizontal division of 1 cm to 0.2 milliseconds. The load consisted of 2.5 gm in this example. The platen 10 was designed to produce a 0.5 millisecond initial shock. About 1,500 G maximum was obtained.

Figure 4:
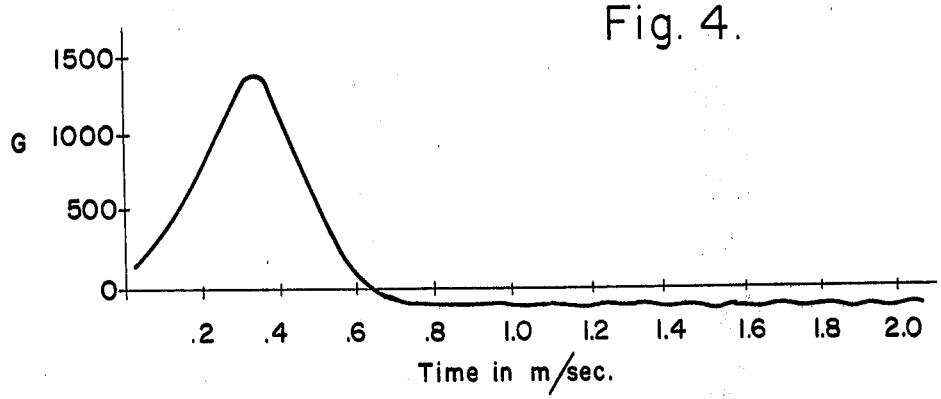

FIG. 4 was taken under the same conditions but with a 2,000 Hz filter provided in the output.

There has thus been disclosed a mechanical shock generating machine. The machine is characterized by a platen which is mechanically insulated from secondary shocks by the provision of a viscous fluid. The viscous fluid will also dampen ringing of the platen and the like. The mechanical shock is generated by a bullet or similar element having a rounded nose which is in free flight; that is, in a ballistic mode. The nose of the bullet impacts a yieldable shock pad which transmits the mechanical shock to the platen. The platen is now capable of moving upwards under the impulse of the shock and against the shear force of the viscous fluid. The bullet may be accelerated by the movable armature of an electromagnet which is briefly excited electronically. The duration of the shock is determined by the thickness of the shock pad, and the G's imparted to the platen are basically determined by the energy of the bullet.

What is claimed is:

1. A mechanical shock generating machine comprising:
   (a) a platen for mounting thereon a component to be shock tested;
   (b) a skirt secured to said platen and depending therefrom;
   (c) a viscous fluid surrounding said skirt for permitting said platen to move in a vertical direction under the influence of a mechanical impact and for dampening ringing of said platen under the influence of said impact;
   (d) a shock pad mounted on the lower surface of said platen for receiving said impact, said shock pad consisting of a yieldable material;
   (e) a metal bullet having a rounded nose;
   (f) means for accelerating said bullet upwards toward said shock pad and in free flight for causing said bullet nose to impact said shock pad, thereby to lift said platen against the viscous action of the fluid; and
   (g) means for stopping the flight of said bullet after it has delivered the mechanical impact to said shock pad.

2. A shock generating machine as defined in claim 1 wherein said means for accelerating includes a magnetic coil, an armature capable of moving upwards under the influence of an applied magnetic field, said bullet being freely disposed on said armature, and a stop for stopping the motion of said armature and permitting said bullet to continue in free flight.

3. A shock generating machine as defined in claim 2 wherein means are provided for applying an alternating current voltage to said coil when said current crosses its zero axis for a predetermined period of time to generate the mechanical impact by said bullet having a duration determined by the thickness of said shock pad generating a shock having a predetermined number of G's determined by the weight of said bullet, its acceleration and the duration of said shock.

4. A mechanical shock generating machine comprising:
   a. a platen for mounting thereon a component to be shock tested;
   b. means connected to said platen including a skirt depending therefrom, said means yieldably supporting said platen,
   c. a bullet-shaped element adapted to be projected in a ballistic mode toward said platen, said platen being arranged to move under the impact of said element;
   d. means for projecting said element with sufficient energy to impart to said platen a predetermined number of G's, and
   e. a viscous fluid surrounding said skirt to insulate said platen from secondary shocks and to dampen possible ringing of said platen.

* * * * *